United States Patent
Roodenko

(10) Patent No.: US 10,458,907 B2
(45) Date of Patent: Oct. 29, 2019

(54) INFRARED ANALYTICAL SENSOR FOR SOIL OR WATER AND METHOD OF OPERATION THEREOF

(71) Applicant: Max-IR Labs, LLC, Dallas, TX (US)

(72) Inventor: Ecatherina Roodenko, Plano, TX (US)

(73) Assignee: MAX-IR LABS, LLC, Dallas, TX (US)

( * ) Notice: Subject to any disclaimer, the term of this patent is extended or adjusted under 35 U.S.C. 154(b) by 0 days.

(21) Appl. No.: 15/990,195

(22) Filed: May 25, 2018

(65) Prior Publication Data

US 2018/0340884 A1 Nov. 29, 2018

Related U.S. Application Data

(60) Provisional application No. 62/512,147, filed on May 29, 2017.

(51) Int. Cl.
| | |
|---|---|
| *G01N 21/3577* | (2014.01) |
| *G01N 21/552* | (2014.01) |
| *H01L 31/101* | (2006.01) |
| *H01L 31/16* | (2006.01) |
| *G01N 21/15* | (2006.01) |
| *G01N 21/35* | (2014.01) |

(52) U.S. Cl.
CPC ....... *G01N 21/3577* (2013.01); *G01N 21/552* (2013.01); *H01L 31/101* (2013.01); *H01L 31/162* (2013.01); *G01N 21/15* (2013.01); *G01N 2021/3595* (2013.01); *G01N 2201/088* (2013.01)

(58) Field of Classification Search
CPC ............ G01N 21/3577; G01N 21/552; G01N 2201/088; G01N 2021/3595; H01L 31/101; H01L 31/162
See application file for complete search history.

(56) References Cited

U.S. PATENT DOCUMENTS

| | | | |
|---|---|---|---|
| 2006/0038990 A1* | 2/2006 | Habib | G01N 21/658 356/301 |
| 2013/0037719 A1* | 2/2013 | Melling | G01N 21/3577 250/340 |
| 2015/0346178 A1* | 12/2015 | Wang | G01N 33/1886 436/52 |

OTHER PUBLICATIONS

Soriano et al., "The Performance of Visible, Near-, and Mid-Infrared Reflectance Spectroscopy for Prediction of Soil Physical, Chemical, and . . . ", Applied Spectroscopy Reviews, Feb. 2014.
Charlton et al., "Infrared Evanescent Field Sensing with Quantum Cascade Lasers and Planar Silver Halide Waveguides", Anal. Chem. 2005, 77, pp. 4398-4403.

(Continued)

*Primary Examiner* — David P Porta
*Assistant Examiner* — Fani Boosalis

(57) ABSTRACT

An infrared (IR) sensor and a method of detecting molecular species in a liquid. In one embodiment, the IR sensor includes: (1) an IR light source configured to emit IR light, (2) a sensing element configured to receive the IR light, the IR light generating an evanescent field about the sensing element as the IR light propagates therethrough, molecules in a subject liquid interacting with the evanescent field and affecting a characteristic of the IR light and (3) an IR light detector configured to receive the IR light from the sensing element and detect the characteristic.

6 Claims, 10 Drawing Sheets

(56) References Cited

OTHER PUBLICATIONS

Dinh et al., "A review on non-dispersive infrared gas sensors: Improvement of sensor detection limit and interference correction", Sensors and Actuators B: Chemical, 2016, p. 529-538.

Davis, T.A., "Donnan Dialysis", Academic Press, 2000, pp. 1701-1707.

Hooda et al., "Determination of Nitrate in Water containing Dissolved Organic Carbon by Ultraviolet Spectroscopy", International Journal of Environmental Analytical Chemistry, May 2001, 13 pages.

Etheridge et al., "Addressing the Fouling of In Situ Ultraviolet-Visual Spectrometers Used to Continuously Monitor Water Quality in Brackish Tidal Marsh Waters", Journal of Environmental Quality, Feb. 15, 2013, pp. 1896-1901.

Hummelgard et al., "Low-cost NDIR based sensor platform for sub-ppm gas detection", Urban Climate, 14 (2015), p. 342-350.

Simonescu, Claudia Maria, "Application of FTIR Spectroscopy in Environmental Studies", Advanced Aspects of Spectroscopy, 2012, 36 pages.

Mizaikoff et al., "Infrared fiber-optical chemical sensors with reactive surface coatings", Sensors and Actuators B 29, 1995, p. 58-63.

Linker et al., "Nitrate Determination in Soil Pastes using Attenuated Total Reflectance Mid-infrared spectroscopy: Improved Accuracy Via Soil Identification", Biosystems Engineering, 2006, pp. 111-118.

Max et al., "Aqueous ammonia and ammonium chloride hydrates: Principal infrared spectra", Journal of Molecular Structure 1046, 2013, pp. 124-135.

Lu et al., "Determination of Chlorinated Hydrocarbons in Water Using Highly Sensitive Mid-Infrared Sensor Technology", Scientific Reports, Jun. 14, 2013, pp. 1-6.

Mizaikoff, Boris, "Recent trends in mid-infrared sensing", Proc. SPIE 4253, Optical Fibers and Sensors for Medical Applications, Jun. 4, 2001, 9 pages.

Vincent et al., "Development of a low-cost NDIR system for ppm detection on carbon dioxide in exhaled breath analysis", ScienceDirect, 2015, pp. 388-391.

Linker, R., "Determination of nitrate in soils using mid-infrared spectroscopy", Technion-Israel Institute of Technology, 2006, 15 pages.

Pandey et al., "The Relative Performance of NDIR-based Sensors in the Near Real-time Analysis of CO2 in Air", Sensors, 2017, 7, pp. 1683-1696.

Pellerin et al., "Optical Techniques for the Determination of Nitrate in Environmental Waters: Guidelines for Instrument Selection, Operation, Deployment, Maintenance, Quality Assurance, and Data Reporting", USGS, 2013, 48 pages.

Raichlin, Y. "Fiber-Optic Evanescent Wave Spectroscopy in the Middle Infrared", School of Physics and Astronomy, vol. 62, No. 2, 2008, 18 pages.

Alexandratos, Spiro D., "Ion-Exchange Resins: A Retrospective from Industrial and Engineering Chemistry Research", Ind. Eng. Chem. Res., 2009, 48 (1) pp. 388-398.

Alai et al., "Sensor Acquisition for Water Utilities: A Survey and Technology List", Lawrence Livermore National Laboratory, Mar. 14, 2005, 24 pages.

Raich, Jordi, "Review of sensors to monitor water quality", European Commission, Dec. 2013, 33 pages.

T.A. Vincent et al., "A low cost MEMS based NDIR system for the monitoring of carbon dioxide in breath analysis at ppm levels", Sensors and Actuators B 236 (2017), pp. 954-964.

Jacob Wong and Chi Tse, "Recalibration technique for NDIR gas sensors with the need for gas standards", Jacob Wong and Chi Tse, Sensor Review, vol. 32, No. 3, 2012, pp. 217-221.

Wong et al., "Zero drift NDIR gas sensors", Sensor Review, Oct. 23, 2017, vol. 31 Issue: 1, pp. 70-77.

\* cited by examiner

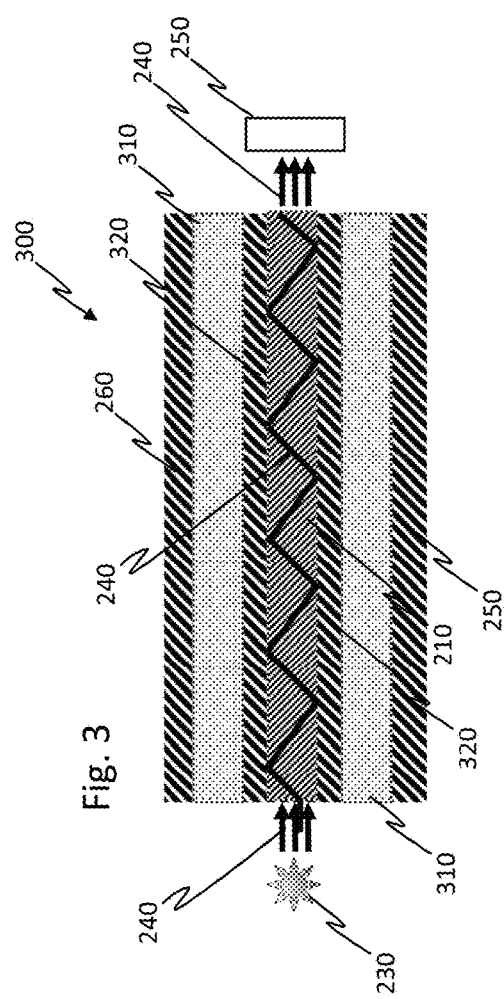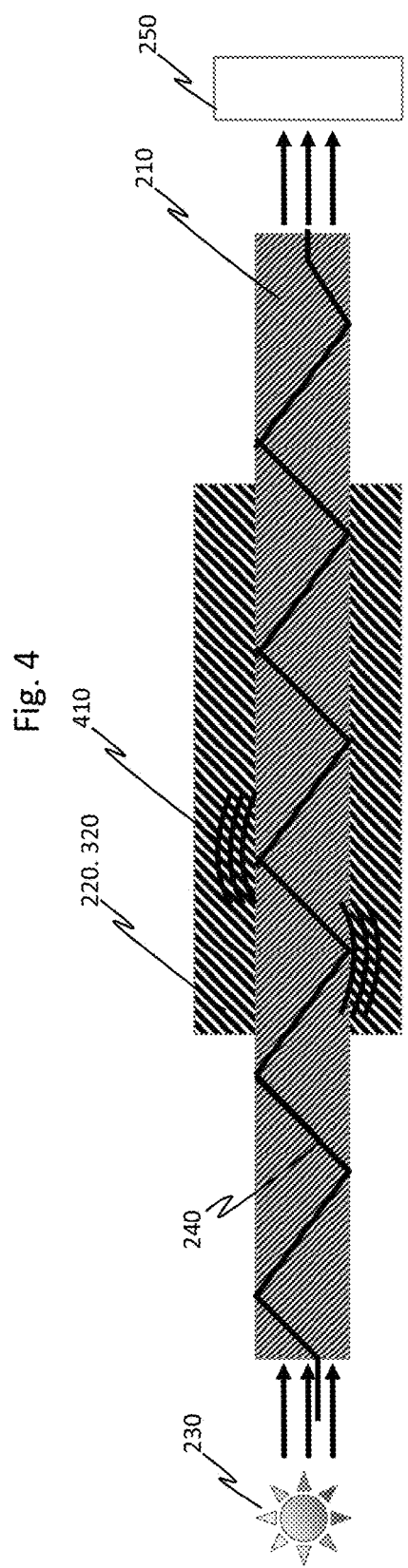

INFRARED ANALYTICAL SENSOR FOR SOIL OR WATER AND METHOD OF OPERATION THEREOF

CROSS-REFERENCE TO RELATED APPLICATION

This application claims the benefit of U.S. Provisional Application Ser. No. 62/512,147, filed by Roodenko on May 29, 2017, entitled "Optical Sensor for Nutrient and Contaminant Detection in Agricultural Soils and Environmental Waters," commonly assigned with this application and incorporated herein by reference.

TECHNICAL FIELD

This application is directed, in general, to chemical sensors and, more specifically, to an infrared (IR) sensor capable of detecting molecular species, and thereby the presence of nutrients or contaminants in agricultural soils or environmental and industrial waters and a method of detecting molecular species in a liquid.

BACKGROUND

Nitrate sensors are becoming increasingly important tools for water and soil quality monitoring and resource management. Ultraviolet (UV) absorption sensors are today's standard for water quality analysis (Pellerin, et al., "Optical Techniques for the Determination of Nitrate in Environmental Waters: Guidelines for Instrument Selection, Operation, Deployment, Maintenance, Quality Assurance, and Data Reporting: U.S. Geological Survey Techniques and Methods," USGS, Vol. 1-D5 (2013), and, Sah, "Nitrate-nitrogen Determination—A Critical Review," Commun. Soil Sci. Plant Anal., vol. 25, pp. 2841-2869 (1994)).

Unfortunately, UV sensors capable of delivering continuous data during prolonged deployment periods not only cost between $15,000 and $25,000, but are also vulnerable to interference from inorganic and organic substances that absorb light at wavelengths similar to those of nitrate. These substances include nitrite, bromide and chromophoric dissolved organic carbon (DOC), which are common in both water and soil.

SUMMARY

One aspect provides an IR sensor and a method of detecting molecular species in a liquid. In one embodiment, the IR sensor includes: (1) an IR light source configured to emit IR light, (2) a sensing element configured to receive the IR light, the IR light generating an evanescent field about the sensing element as the IR light propagates therethrough, molecules in a subject liquid interacting with the evanescent field and affecting a characteristic of the IR light and (3) an IR light detector configured to receive the IR light from the sensing element and detect the characteristic.

In another embodiment, the IR sensor includes: (1) an IR light source, (2) an optical fiber configured to receive IR light from the IR light source, (3) a selective ion-exchange (IX) medium associated with the optical fiber, the IR light generating an evanescent field about the optical fiber as the IR light propagates therethrough, the selective IX medium configured to transport an ion species in a subject liquid about the optical fiber and (4) an IR light detector configured to receive the IR light from the optical fiber, the ion species affecting the evanescent field and thereby a characteristic of the IR light.

Another aspect provides a method of detecting molecular species in a liquid. In one embodiment, the method includes: (1) propagating IR light through a sensing element, the propagating generating an evanescent field about the sensing element, molecules in a subject liquid proximate the sensing element interacting with and affecting the evanescent field; and (2) detecting a characteristic of the IR light affected by the evanescent field.

BRIEF DESCRIPTION OF THE DRAWINGS

Reference is now made to the following descriptions taken in conjunction with the accompanying drawings, in which:

FIG. 3 schematically shows a cross-section of one embodiment of an IR sensor employing an optical fiber and a permselective membrane as the selective IX medium;

FIG. 4 schematically shows IR detection using the IR sensor;

DETAILED DESCRIPTION

As stated above, nitrate sensors are becoming increasingly important tools for water and soil quality monitoring and resource management. In water, excess nutrients, particularly nitrogen and phosphorus, can trigger algal blooms and biodiversity loss with consequences that affect the economy and pose a threat to human health. The cost of freshwater nutrient pollution in the United States alone has been estimated at US$2.2 billion per year (Dodds, et al., "Eutrophication of U.S. Freshwaters: Analysis of Potential Economic Damages," Environ. Sci. Technol., vol. 43, pp. 12-19 (2009)).

In agriculture, nitrogen fixing in soils accounts for over 60% of global, water-soluble fertilizer market share, but approximately 30% of the fertilizer applied to North American soils is wasted due to overapplication and runoff. With U.S. farmers spending US$12 billion annually on fertilizer, nitrate sensors could be used to reduce fertilizer consumption and cost substantially, as well as the labor and fuel costs associated with fertilizer application.

As stated above, while UV absorption sensors are today's standard for water quality analysis, they are expensive and vulnerable to interference from common inorganic and organic substances. These shortcomings have significantly limited their application and use.

It is realized herein that components that function in the IR spectral range may be combined to form an IR sensor. Such components may be commercially available at little cost. Many of the embodiments are suitable to detect nutrients or contaminants in either soils or waters, which makes them particularly attractive for agricultural, environmental and residential or industrial wastewater treatment use. Given their potentially low cost, the embodiments are particularly amenable for forming sensor networks, in which each sensor transmits its data to a central site for storage and likely further analysis. Indeed, such networks may be capable of delivering new kinds of analysis and tactical and strategic services to farmers, conservationists, operators of water works and public safety or national security agencies.

It is more specifically realized herein that a commercially available selective IX medium (e.g., an IX resin coating or permselective membrane) may be used in conjunction with a sensing element (e.g., an optical fiber or coated wafer) to yield an IR sensor which, in many embodiments, has a range of sensitivity from 0.001 ppm to 100 ppm, and beyond, at a price far lower than conventional UV sensors.

Embodiments of the IR sensor illustrated and described herein employ selective IX medium appropriate for sensing nitrate. However, those skilled in the pertinent art will, with the benefit of this disclosure, understand that alternative or additional selective IX media may be employed in the sensor to allow it to sense corresponding alternative or additional nutrients (e.g., nitrogen, phosphorus, sulfate, or potassium) or contaminants (e.g., arsenic).

Figure 1A:
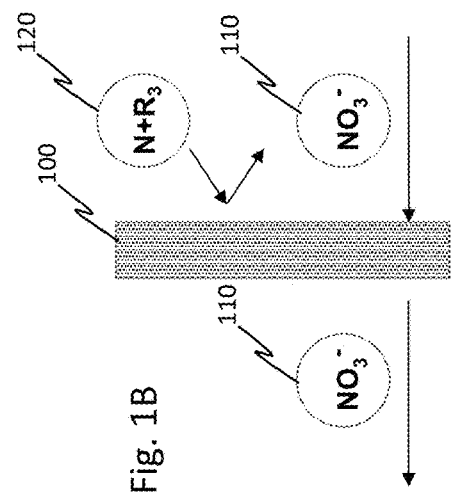
FIG. 1A schematically shows a selective IX medium with $NO_3$ anions and quaternary ammonium cations shown as $N^+R_3$.

FIG. 1A schematically shows a selective IX medium 100 by itself, with $NO_3$ anions (e.g., an $NO_3$ anion 110) and quaternary ammonium cations shown as $N^+R_3$ (e.g., an $N^+R_3$ cation 120).

Figure 1B:
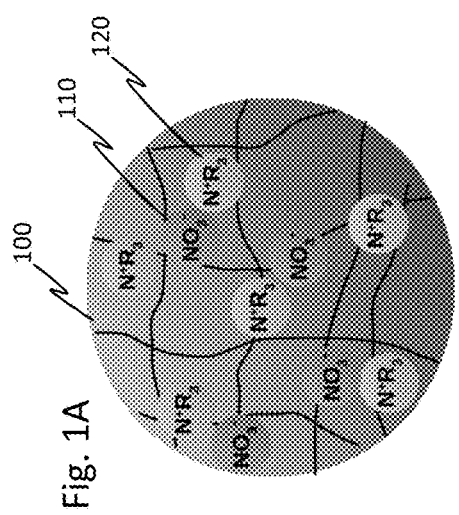
FIG. 1B schematically shows how the selective IX medium of FIG. 1A functions.

Assuming the selective IX medium 100 to be an anion-exchange membrane, FIG. 1B schematically shows how the anion-exchange membrane 100 of FIG. 1A functions. First, a definition is in order. "Subject liquid" is defined herein as a liquid that the IR sensor has measured, is measuring or will be measuring. In real-world applications, the subject liquid will usually be water containing dissolved nutrients or contaminants. In the context of environmental waters or residential or industrial wastewaters, the subject liquid may be the waters themselves or the waters following some particulate filtration. In the context of agricultural soils, the subject liquid is typically water drained from or filtered through the soil.

Given this definition, a subject liquid (e.g., environmental water or soil drainage), perhaps containing $NO_3$ anions 110 and $N^+R_3$ cations 120, is placed in contact with one side of the anion-exchange membrane 100 (e.g., the right-hand side of the anion-exchange membrane 100 as FIG. 1B is oriented). The net negative charge of the $NO_3$ anion 110 attracts it to the anion-exchange membrane 100, causing the $NO_3$ anion 110 to absorb, and perhaps pass entirely through, it. In contrast, the net positive charge of the $N^+R_3$ cation 120 repels it from the anion-exchange membrane 100, dissuading the $N^+R_3$ cation 120 from absorbing or passing through it. A cation-exchange membrane acts in the opposite manner, attracting and absorbing cations and repelling anions.

Figure 2:
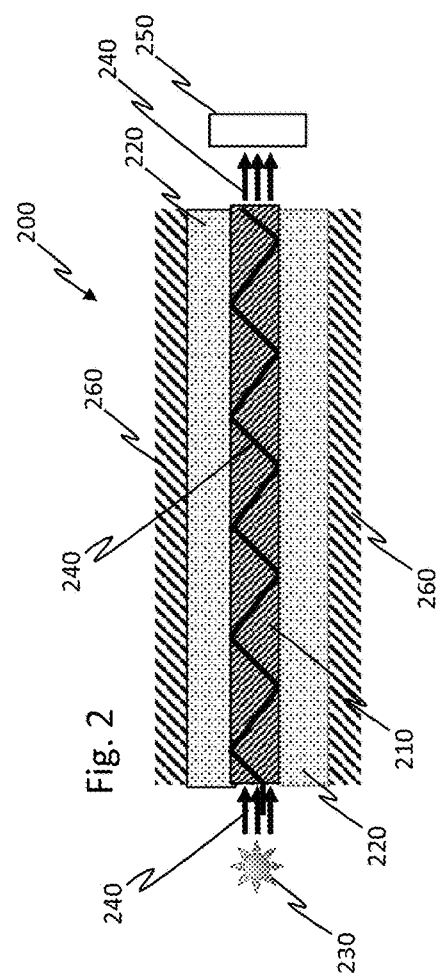
FIG. 2 schematically shows a cross-section of one embodiment of an IR sensor employing an optical fiber and an ion-exchange coating as the selective IX medium.

FIG. 2 schematically shows a cross-section of one embodiment of an IR sensor 200 employing an optical fiber 210 and an IX coating 220 as the selective IX medium 100 of FIG. 1B. An IR source 230, which may include a commercially-available IR laser diode, quantum cascade laser (QCL) or thermal emitter, emits IR light 240, which is directed into an end of the optical fiber 210. The optical fiber 210, which may be a commercially-available optical fiber, serves as a waveguide for the IR light 240. Accordingly, the IR light 240 reflects off a boundary surface of the optical fiber 210 as it propagates therethrough. A sawtooth line shown in the optical fiber 210 represents this propagation and reflection in FIG. 2. As those skilled in the pertinent art understand, the propagation and reflection of the IR light 240 through the optical fiber 210 creates an evanescent field (not shown in FIG. 2) surrounding the optical fiber 210.

An IR detector 250, which may include a commercially-available thermal or photonic detector, receives the propagated IR light 240 from an end of the optical fiber 110 and produces an electrical signal as a function thereof. The IR detector 250 may include signal processing hardware, perhaps operating under the control of software or firmware, to receive and process the electrical signal in some manner. In many embodiments, the electrical signal is analyzed to determine amplitude attenuation indicating IR light absorption occurring as a function of molecular species (e.g., ion) concentration proximate the sensing element (the optical fiber 210 in the embodiment of FIG. 2). The IR detector 250 may further include communication circuitry configured to transmit the electrical signal or a processed form of the electrical signal, perhaps in digital form and perhaps for remote, centralized collection and analysis.

In various alternative embodiments, the resin employed to form the IX coating 220 may be: (1) purchased commercially from ResinTech, Inc., of West Berlin, N.J., (2) purchased commercially from the Dow Chemical Company of Midland, Mich., under the trademark Dowex® or Amberlite®, or (3) manufactured in accordance with Eyal, et al., "Nitrate-selective Anion-exchange Membranes," J. Membrane Sci., vol. 38.2, pp. 101-111 (1988).

In the embodiment of FIG. 2, the IX coating 220 covers the full circumference of the optical fiber 210. In alternative embodiments, the IX coating 220 covers less than the full circumference of the optical fiber 210. In the IR sensor 200, the IR source 230 and IR detector 250 are located proximate opposing ends of the optical fiber 210. In alternative embodiments, the IR source 240 and IR detector 250 are located at the same end of the optical fiber 210, a mirror (not shown) is located proximate the opposing end of the optical fiber 210, and the IR light 240 propagates twice through the optical fiber 210. In the embodiment of FIG. 2, the optical fiber 210 serves as the sensing element. In an alternative embodiment, a coated wafer, formed by depositing an IR-transparent material (e.g., nanocrystalline diamond) on a silicon wafer, serves as the sensing element. Coated wafers are commercially available, for example, from Diamond Materials GmbH of Freiburg, Germany.

The IX coating 220 and optical fiber 210 are placed in a subject liquid 260, causing the subject liquid 260 to surround the IX coating 220. Consequently, the IX coating 220 absorbs at least some of any $NO_3$ contained in the subject liquid 260 and transports the $NO_3$ toward the optical fiber 210. An evanescent field projects from the surface of the optical fiber 210 and interacts with the transported or absorbed $NO_3$. The IX coating 220 prevents fouling and interfering agents (such as particles or other chemical components) from substantially interacting with the evanescent field.

FIG. 3 schematically shows a cross-section of one embodiment of an IR sensor 300 employing an optical fiber 210 and a permselective membrane 310 as the selective IX medium 100 of FIG. 1B. The IR sensor 300 has many elements in common with the IR sensor 200, so like reference numerals designate like elements. However, in FIG. 3, a gap exists between the optical fiber 210 and the permselective membrane 310, creating a volume 320. The permselective membrane 310 absorbs at least some of any $NO_3$ contained in the subject liquid 260 and transports the $NO_3$ into the volume 320. The permselective membrane 310 prevents fouling and interfering agents from substantially interacting with the evanescent field.

The IR sensor 200 of FIG. 2, with its IX coating 220 is a simpler design than the IR sensor 300, because the IX coating 220 directly covers the optical fiber 210, and its performance is well-defined. However, the resin composing the IX coating 220 may require occasional regeneration. Further, continuous measurement of $NO_3$ concentrations when $NO_3$ concentrations decrease over time typically requires the establishment of a proper reference. A sub-cell (not shown) may need to exist in the IR sensor 200 to provide the measurements required to establish a reference. This approach is widely used in gas sensors that employ non-dispersive IR (NDIR) detection, which will be described below. In an alternative embodiment, the optical fiber 210 with its IX coating 220 may be considered a disposable and replaceable element. This alternative embodiment may be particularly advantageous for a portable or hand-held water or soil sensor.

The IR sensor 300 of FIG. 3, with its permselective membrane 310 is a more complex design than the IR sensor 200, because it requires the additional volume 320. The permselective membrane 310 has at least two embodiments for $NO_3$ transport: (1) electrochemical and (2) transport by means of Donnan dialysis, which uses counter diffusion of two or more ions through an IX membrane to achieve separation. Electrochemical transport requires external power, while Donnan dialysis does not. Donnan dialysis is therefore preferable for applications requiring continuous data collection by widely or remotely deployed IR sensors.

An alternative embodiment, which requires no additional illustration due to its simplicity, dispenses with the selective IX medium, whether it take the form of an IX coating as in the IR sensor 200 or a permselective membrane as in the IR sensor 300. Thus, the optical fiber is positioned in direct contact with the subject liquid. While this embodiment is vulnerable to interference from inorganic and organic substances that absorb light at wavelengths similar to those of nitrate, one or both of an optical filter or spectrometer may be employed to define a specific spectral range of operation. If a spectrometer is employed, the principles of detection are, of course, spectroscopic rather than NDIR.

FIG. 4 schematically shows IR detection using the IR sensor. More particularly, FIG. 1D shows a region (which may be the anion-exchange membrane 220 of FIG. 2 or the volume 320 of FIG. 3) proximate the optical fiber 110 and an evanescent field 410 created as the IR light 240 propagates through the optical fiber 210 and reflects off its boundary layer (not shown). (An evanescent field is sometimes referred to as a "leaky mode" or "tunneling waves.") At least some of the $NO_3$ in the region 220, 320 lies within the evanescent field 410. The $NO_3$ interacts with the evanescent field 410, absorbing some of it and thereby changing the optical characteristics of the IR light 240 propagating through the optical fiber 210. The change is a function of the concentration of the $NO_3$. The IR detector 250 is configured to detect the changes in the optical characteristics and produce an electrical signal indicative thereof.

The theory of operation of the IR sensor is based on IR fiber-optic evanescent field sensing (FEWS) (Katzir, et al., "IR Fiber-Optic Evanescent Wave Spectroscopy (FEWS) for Sensing Applications (Conference Presentation)," In Proc. SPIE 9703; p. 970308, and, Raichlin, et al. "Flattened Infrared Fiber-Optic Sensors for the Analysis of Micrograms of Insoluble Solid Particles in Solution or in a Dry State," Vib. Spectrosc. 2014, vol. 73, pp. 67-72).

FEWS is similar to attenuated total reflection (ATR) sensing, which is widely used. In ATR, light is totally internally reflected within a sensing element. In the presence of a medium above the sensor surface (such as the anion-exchange membrane 220 of FIG. 2 or the volume 320 of FIG. 3), the evanescent field is coupled into this medium with a penetration depth of a few micrometers, depending on the refractive index of the materials involved, operating wavelength and the angle of incidence of the light forming the evanescent field.

The selective IX medium performs several important functions in the IR sensor 100. First, the selective IX medium substantially prevents fouling (Etheridge, et al., "Addressing the Fouling of In Situ Ultraviolet-Visual Spectrometers Used to Continuously Monitor Water Quality in Brackish Tidal Marsh Waters," J. Environ. Qual., vol. 42, p. 1896, (1986)) caused by biological growth or chemical precipitation in the context of environmental waters and agricultural soils, particularly over long deployment periods. The film/resin/membrane in this case functions as a barrier that separates any fouling agents away from the sensing element, protecting the light propagating through it from interacting with them.

Second, by preferentially absorbing/transporting $NO_3$ ions, the selective IX medium filters out inorganic and organic substances having overlapping absorption bands. This is useful, because it enables NDIR detection (Wong, et al., "Non-Dispersive Infrared Gas Measurement," IFSA Publishing (2012), and, Wong, et al., "Recalibration Technique for NDIR Gas Sensors without the Need for Gas Standards," Sens. Rev., vol. 32, pp. 217-221 (2012)) and avoids the need for a costly and bulky IR spectrometer. Preliminary results obtained from soil extract samples indicate a unique $NO_3$ signature in the IR spectral range having a peak at about 1342 $cm^{-1}$. One particularly advantageous aspect of the IR sensor described herein is that this peak lies away from the absorption bands caused by unwanted inorganic and organic substances.

NDIR is well-accepted and extensively used in low-cost commercial gas sensors (e.g., Wong, et al., supra). A typical NDIR gas sensor has an IR source, a sample chamber and an IR detector, and often passes the IR light through a wavelength-selective (gas-selective) optical filter. The sample chamber is filled with a gas, and the IR light passes from the IR source, through the sample chamber and to the IR detector, which produces a signal that is processed to indicate absorbed intensity. The well-known Beer-Lambert law (or Beer's law) may then be used to calculate the concentration of the gas from the absorbed intensity. However, aqueous environments present significant IR absorption challenges, which, to date, have prevented NDIR from being used in soil and water applications.

Conventional NDIR can be adapted in a nonobvious way to permit its use in aqueous environments. FIGS. 5A-5D show an NDIR-type sensor adapted for water and soil applications and associated filter meshes for the soil application.

Figure 5:
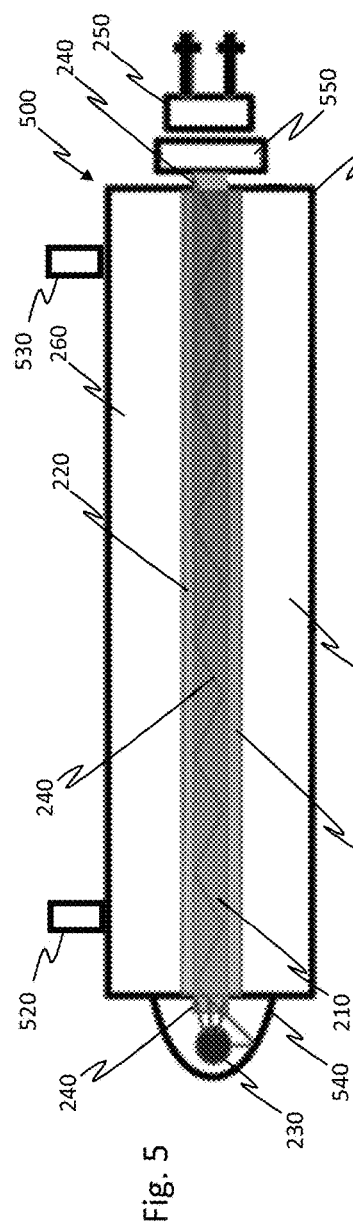
FIG. 5 is a cross-sectional view of one embodiment of an IR sensor configured for analyzing water.

FIG. 5 is a cross-sectional view of one embodiment of an IR sensor 500 configured for analyzing subject liquid. As with the IR sensor 300 of FIG. 3, the IR sensor 500 has many elements in common with the IR sensor 200 of FIG. 2, so like reference numerals designate like elements. The IR sensor 500 has an outer case 510, which contains the subject liquid 260 that surrounds the optical fiber 210 and the anion-exchange membrane 220. The anion-exchange membrane may be an IX coating as in the IR sensor 200 of FIG. 2 or a permselective membrane as in the IR sensor 300 of FIG. 3. The outer case 510 has an inlet 520 and an outlet 530 to accommodate subject liquid flow into and out of the outer case 510. An end cap 540 surrounds and protects the IR source 230 and, in some embodiments, has a mirrored inner surface (not separately referenced) allowing it to function as a reflector. In one specific embodiment, the mirrored inner surface of the end cap 540 has a parabolic shape, and the IR source 230 is located at least proximate the focus of the mirrored inner surface. As a result, IR light emitted by the IR source in any direction other than toward the end of the optical fiber 210 is reflected toward the end of the optical fiber 210. In some embodiments, a wavelength-selective optical filter 550 interposes an end of the optical fiber 210 and the IR detector 250 to select the wavelength that yields the most accurate data regarding the concentration of $NO_3$ anions (or any other nutrient, contaminant or combination thereof that a particular IR sensor 500 may be configured to detect).

Figure 6:
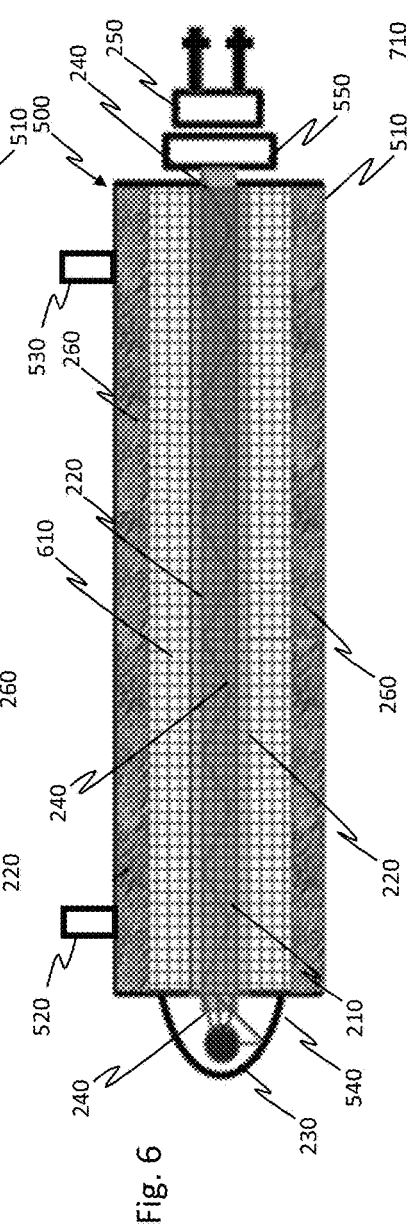
FIG. 6 is a cross-sectional view of one embodiment of an IR sensor embodiment configured for analyzing soil.

FIG. 6 is a cross-sectional view of one embodiment of an IR sensor 600 configured for analyzing soil. As with the IR sensor 500 of FIG. 5 and the IR sensor 300 of FIG. 3, the IR sensor 600 has many elements in common with the IR sensor 200 of FIG. 2, so like reference numerals designate like elements. In fact, the only difference between the illustrated embodiment of FIG. 6. and that of FIG. 5 is the addition of at least one cylindrical filter mesh 610 surrounding the optical fiber 210 and the anion-exchange membrane 220. The cylindrical filter mesh 610 is configured to reduce the number of soil particles that can contact and damage the anion-exchange membrane 220.

Figure 7B:
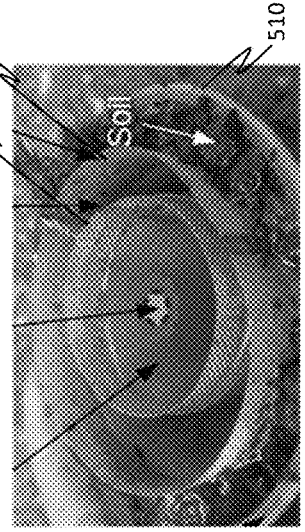
FIG. 7B is an isometric view of concentric filter meshes installed in soil.
Figure 7A:
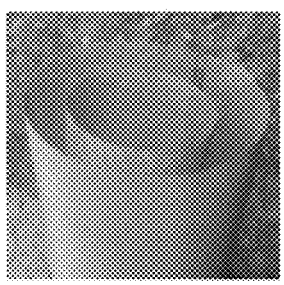
FIG. 7A is a partial isometric view of one embodiment of concentric filter meshes for filtering soil.

Some embodiments of the IR sensor 600 include multiple, concentric cylindrical filter meshes. FIG. 7A is a partial isometric view of one embodiment of concentric cylindrical filter meshes 710, 720 for filtering soil. FIG. 7B is an isometric view of the concentric cylindrical filter meshes 710, 720 installed in soil (unreferenced). FIG. 7B also shows the outer case 510 of the IR sensor 600 and unreferenced soil located between the cylindrical filter mesh 720 and the outer case 510.

Figure 8:
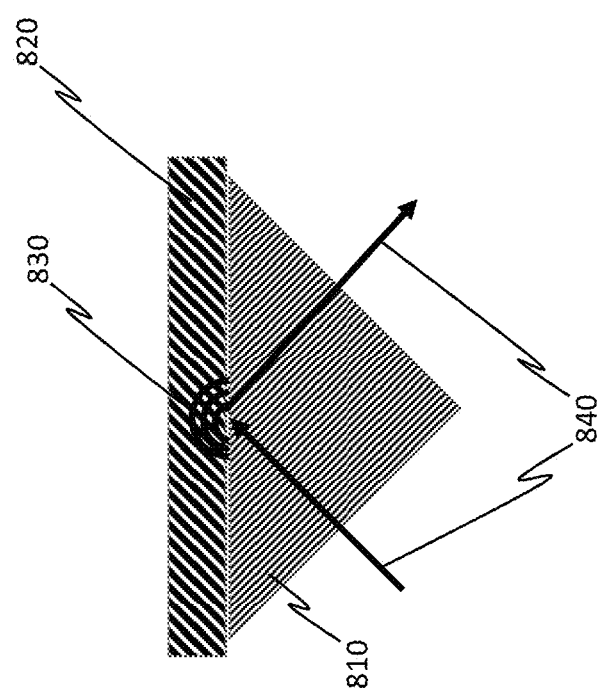
FIG. 8 is a cross-sectional schematic illustration of a test apparatus for demonstrating the feasibility of an IR sensor constructed according to the description herein.

To demonstrate the feasibility of the proposed approach, preliminary tests were performed on water and soil samples using a "single bounce" test apparatus as illustrated in FIG. 8. The apparatus employed an attenuated total reflectance (ATR) element (specifically a Smart iTR™ ATR sampling accessory commercially available from Thermo Fisher Scientific, Inc., of Waltham, Mass.) as a sensing element 210. The sensing element 810 was built into a Fourier transform IR (FTIR) spectrometer (specifically an iS™ 50R FTIR spectrometer also commercially available from the aforementioned Thermo Fisher Scientific), which served as an IR detector (not shown). Both ATR and FEWS employ evanescent field sensing, therefore they were regarded as equivalent for purposes of these tests. A sample (an aqueous solution, or IX medium) 820 was placed adjacent an unreferenced reflection surface of the sensing element 810, and within an evanescent field 830 generated when IR light 840 was caused to propagate through and reflect off the reflection surface of the sensing element 810.

Figure 9B:
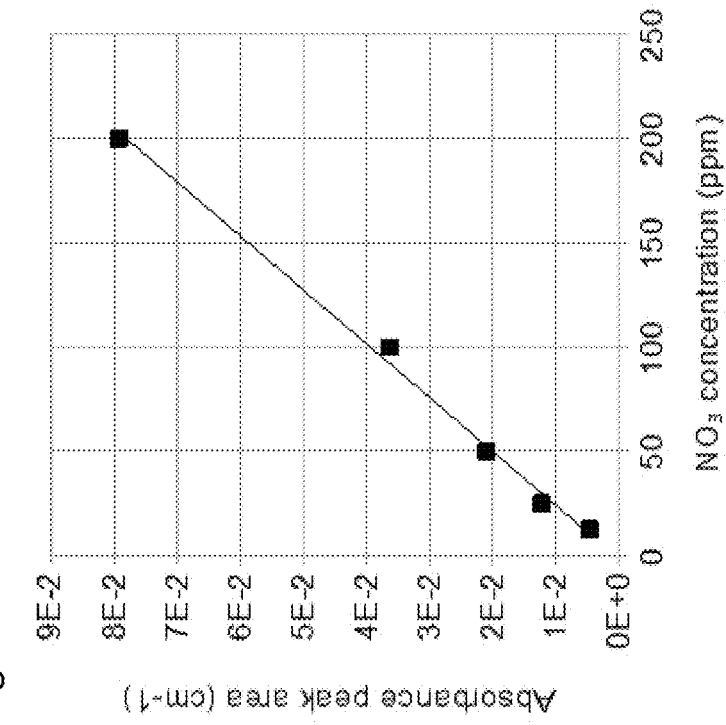
FIG. 9B is a graph illustrating absorbance peaks as a function of $NO_3$ concentration.
Figure 9A:
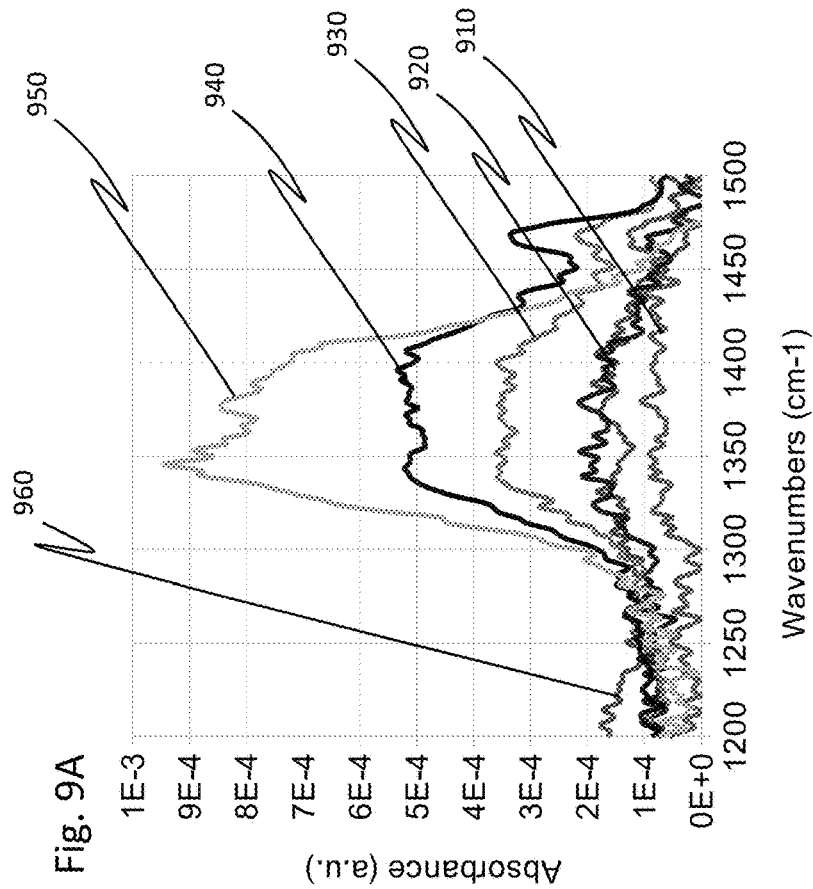
FIG. 9A is a graph illustrating ATR measurements of nitrate dissolved in water (at concentrations of 12.5 ppm to 200 ppm) and data obtained from a solution extracted from soil.

FIGS. 9A and 9B show data obtained from nitrate standard solutions (commercially available from Sigma-Aldrich Corporation, of St. Louis, Mo.) at concentrations of 12.5 ppm (a curve 910), 25 ppm (a curve 920), 50 ppm (a curve 930), 100 ppm (a curve 940) and 200 ppm (a curve 950). A curve 960 shows data obtained from a soil-extracted solution (specifically garden soil) for comparison. FIG. 9B demonstrates a linear dependence between $NO_3$—N concentration and peak area. Independent investigation of $NO_3$—N concentration in this sample of the soil-extracted solution by a colorimetric technique was found to agree with the FTIR data, showing a concentration of 25 ppm.

The data in FIG. 9A demonstrates that the detection of 12.5 ppm of nitrate (the curve 910) is by no means the limit, and the detection sensitivity can be well in the single-digit ppm range. A multi-bounce test apparatus is expected to have a greater sensitivity.

While the well-defined nitrate absorption band obtained from the soil sample of the curve 960 seems to justify foregoing a selective IX medium, the problem of interfering absorption bands from inorganic and organic substances that absorb light at wavelengths similar to those of nitrate becomes more prominent when the experiments are carried out in the field, both in soil and in environmental waters. In field applications one needs to take into account the attenuation of IR light radiation due to fouling that comes from suspended particles and chemical precipitations. This attenuation may be mistakenly interpreted as resulting from $NO_3$ absorption. Therefore, a selective IX medium is important in applications for which spectroscopic detection is impractical.

Figure 10:
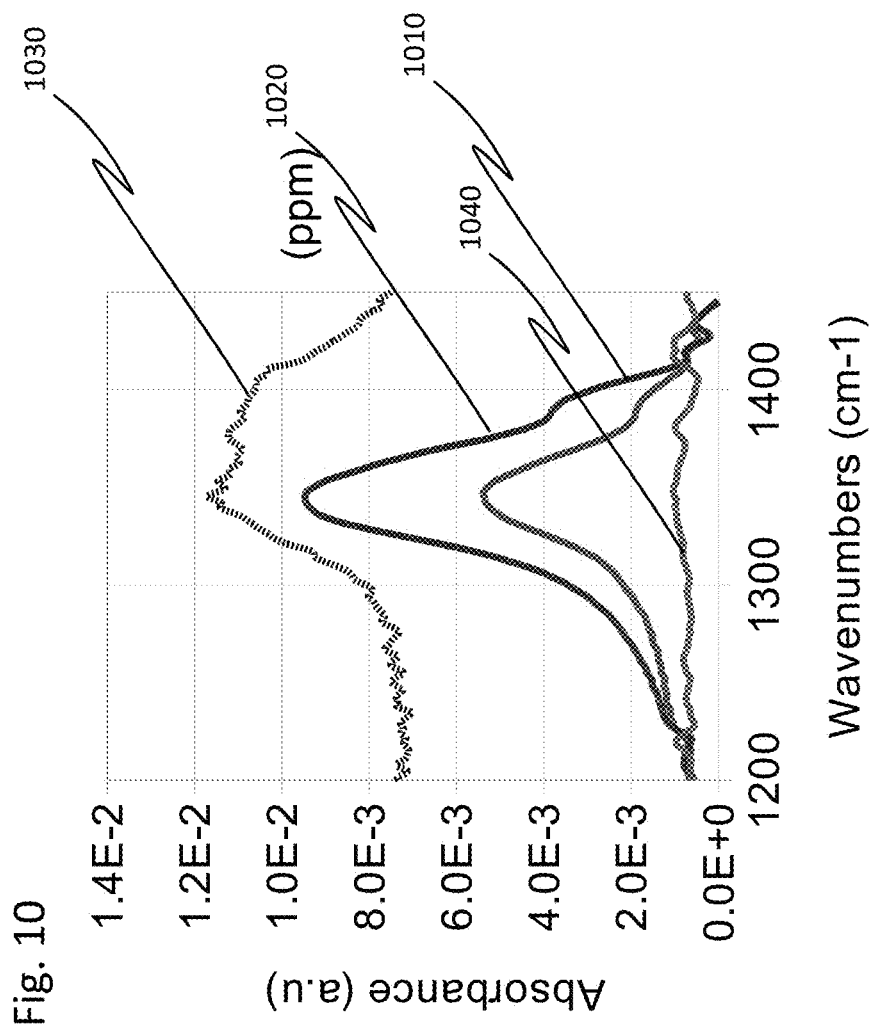
FIG. 10 is a graph illustrating ATR measurements of nitrate dissolved in water and absorbed in an IX resin for 30 minutes.
Figure 11A:
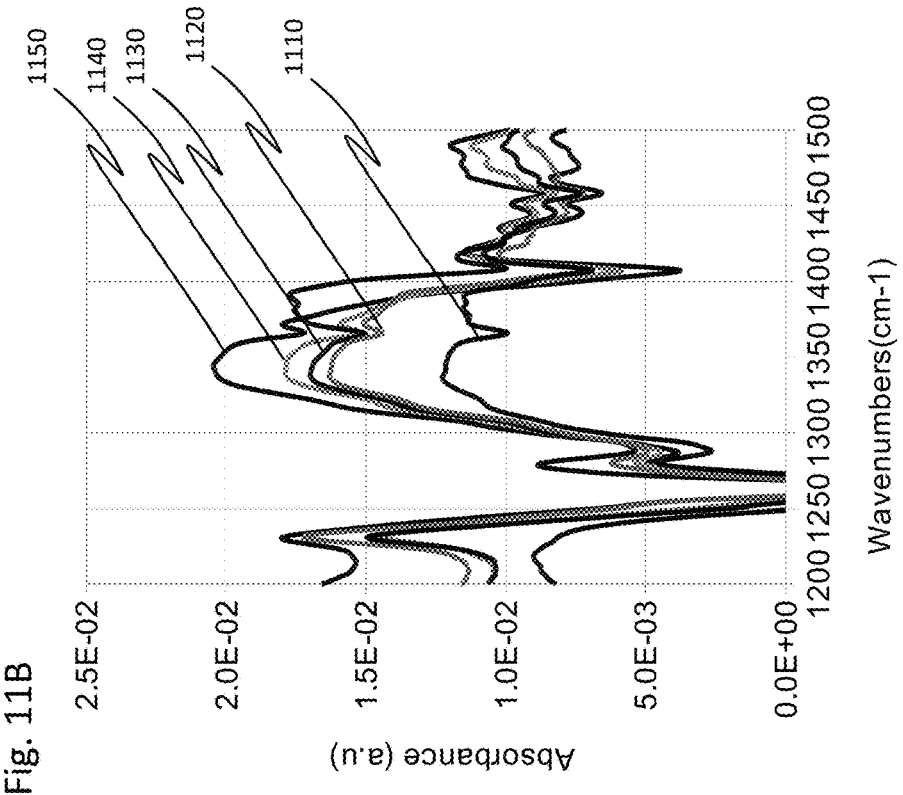
FIGS. 11A-11D are graphs illustrating ATR measurements of nitrate dissolved in water and absorbed in an IX membrane at concentrations of 12 ppm, 25 ppm, 50 ppm and 100 ppm, respectively.
Figure 11B:
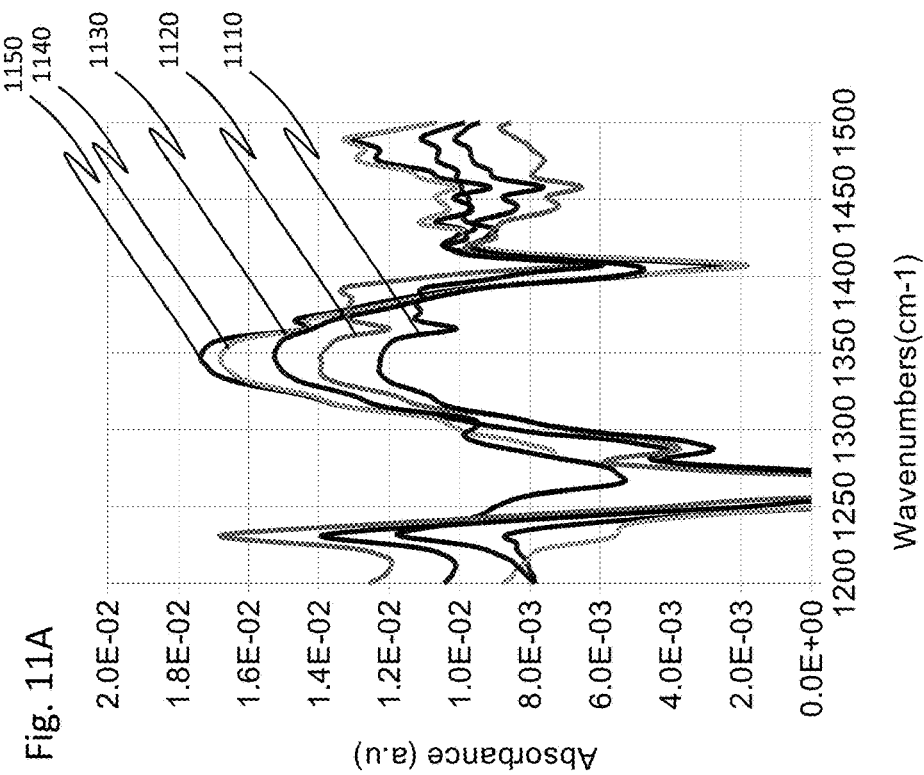
Figure 11C:
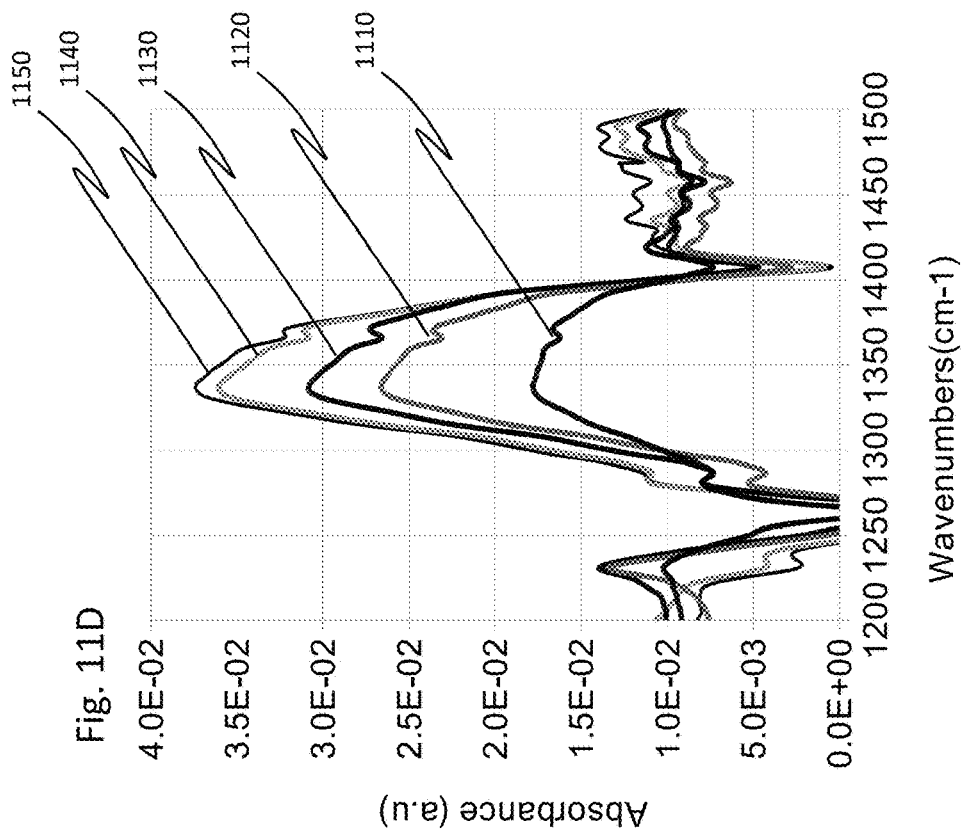
Figure 11D:
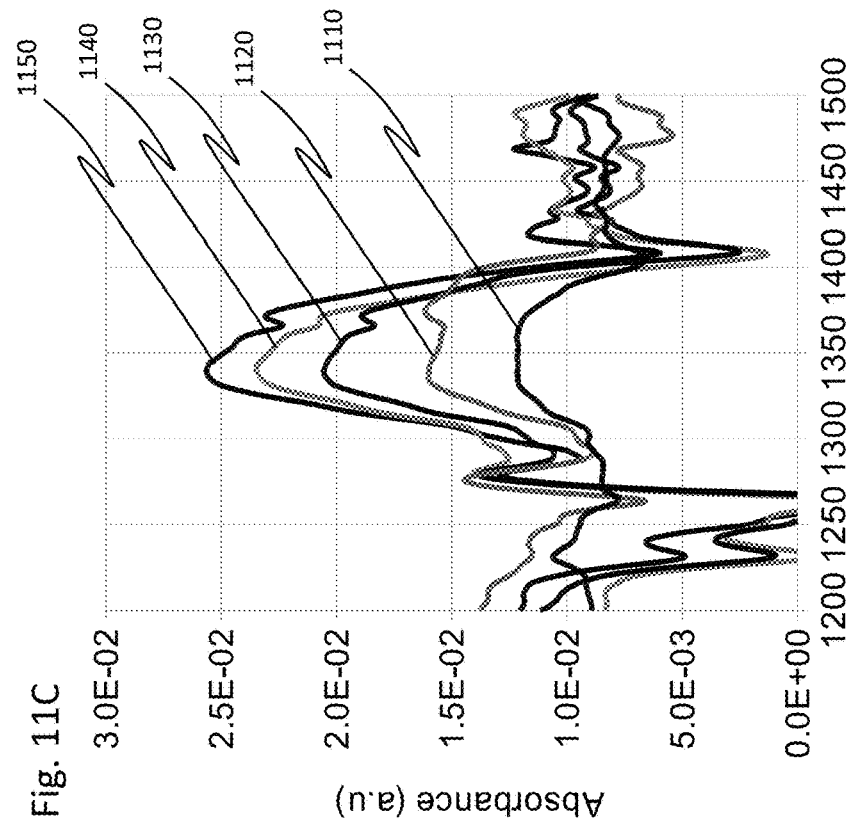

FIG. 10 shows data obtained from Amberlite IRA-400 (CL) IX resin soaked in $NO_3$ at concentrations of 100 ppm (a curve 1010) and 200 ppm (a curve 1020) for 30 min. After that, the resin was washed in water (without any detectable nitrate levels) for 10 min. For comparison, data obtained from resin soaked in water is also shown (a curve 1030), where the peak due to the $NO_3$ is absent.

All data shown in FIG. 10 was referenced to data obtained from resin pre-soaked in water for 10 min. A dashed spectrum (a curve 1040) shows a comparison to the data obtained from 200 ppm $NO_3$—N dissolved in an aqueous solution. The spectrum was plotted with a vertical shift for clarity. The net absorbance value due to the $NO_3$ appears to be stronger in resin than in the water, which is merely the effect of the penetration depth difference inherent in pressed resin particles versus aqueous drops. The $NO_3$ peak appears to be sharper in the resin, with the peak at 1385 cm−1 visible as a shoulder. This is due to an overlap with the disappearing (diminishing) absorption band due to ion exchange. In the proposed instrument, this effect can be treated using an appropriate calibration procedure and algorithms. This illustrates the importance of calibration routines, which should be applied separately to each material when designing a particular sensor. In addition, the form of the resin (film, membrane or particle) and its contact with the sensor are important, as it dictates the strength of the obtained peak.

Figure 12:
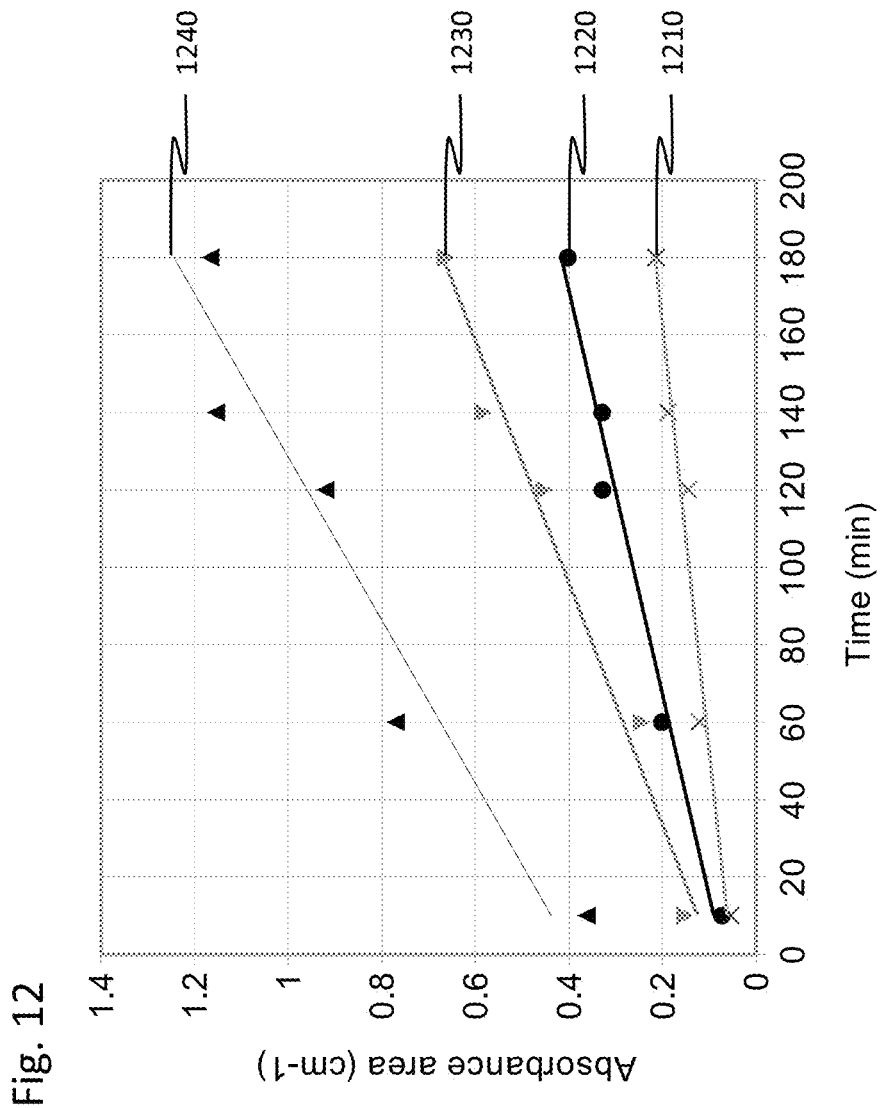
FIG. 12 is a graph illustrating the evolution of $NO_3$ peak areas represented in the graphs of FIGS. 11A-11D as a function of time.

FIGS. 11A-11D show time-series data obtained from $NO_3$ at concentrations of 12 ppm (FIG. 11A), 25 ppm (FIG. 11B), 50 ppm (FIG. 11C) and 100 ppm (FIG. 11D) absorbed in a membrane over intervals of 10 min. (curves 1110), 60 min. (curves 1120), 120 min. (curves 1130), 140 min. (curves 1140) and 180 min. (curves 1150). For these tests, the membrane was immersed into an $NO_3$ solution for specified periods of time, then thoroughly washed in water to prevent any excess drops of $NO_3$ solution on the sensor. The ion exchange within the membrane is evident from the growth of the peak in all of the presented plots. FIG. 12 summarizes the areas of the peaks as a function of time for concentrations of 12.5 ppm (a curve 1210), 25 ppm (a curve 1220), 50 ppm (a curve 1230) and 100 ppm (a curve 1240).

Figure 13:
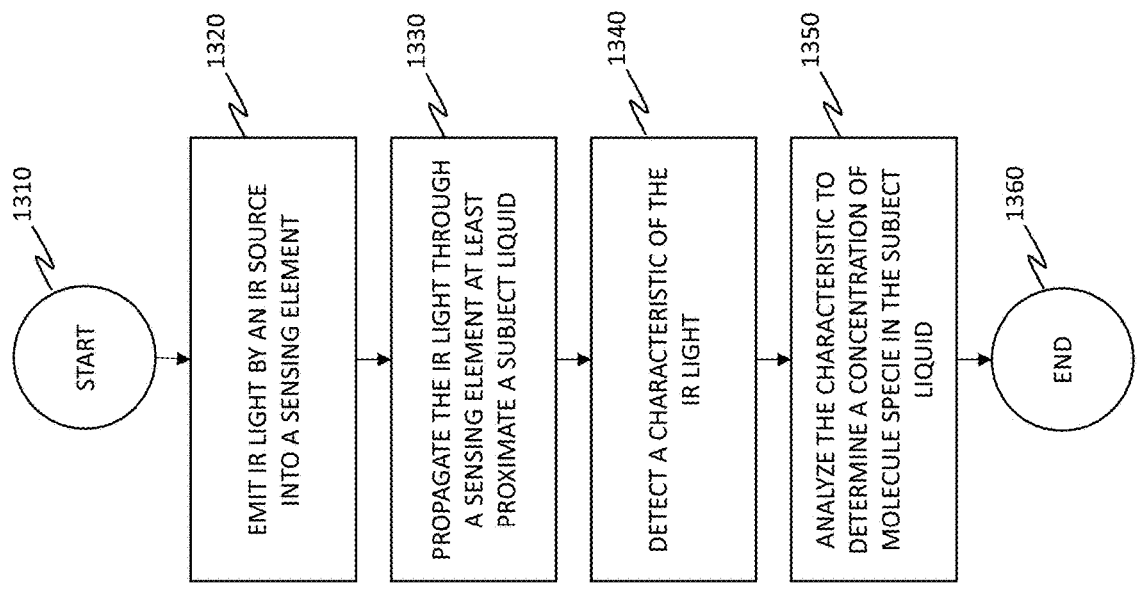
FIG. 13 is a flow diagram of one embodiment of a method of IR detecting molecular species in a liquid.

FIG. 13 is a flow diagram of one embodiment of a method of detecting nutrients and contaminants in agricultural soils or environmental waters. The method begins in a start step 1310. In a step 1320, IR light is emitted by an IR source into a sensing element. In a step 1330, the IR light is propagated through the sensing element. The propagating generates an evanescent field about the sensing element, and molecules (e.g., ions) in a subject liquid at least proximate the sensing element interact with and affect the evanescent field and thereby affect a characteristic of the IR light propagating through the sensing element. In a step 1340, the characteristic is detected. In a step 1350, the characteristic is analyzed to determine a concentration of molecular species (e.g., ions) in the subject liquid. The method ends in an end step 1360.

Those skilled in the art to which this application relates will appreciate that other and further additions, deletions, substitutions and modifications may be made to the described embodiments.

What is claimed is:

1. An infrared (IR) sensor, comprising:
   an IR light source;
   an optical fiber configured to receive IR light from said IR light source;
   a selective ion-exchange (IX) medium associated with said optical fiber, said IR light generating an evanescent field about said optical fiber as said IR light propagates therethrough, said selective IX medium configured to transport an ion species in a subject liquid about said optical fiber; and
   an IR light detector configured to receive said IR light from said optical fiber, said ion species affecting said evanescent field and thereby a characteristic of said IR light.

2. The IR sensor as recited in claim 1 wherein said selective IX medium is selected from the group consisting of:
   an IX resin coating,
   a permselective membrane, and
   an ion-exchange film.

3. The IR sensor as recited in claim 2 wherein said IR detector is selected from the group consisting of:
   a thermal detector, and
   a photonic detector.

4. The IR sensor as recited in claim 2 further comprising an outer case surrounding at least said optical fiber.

5. The IR sensor as recited in claim 4 further comprising at least one filter mesh located within said outer case and surrounding said sensing element.

6. The IR sensor as recited in claim 2 further comprising a wavelength-selective optical filter interposing said optical fiber and said IR detector.

* * * * *